US011864893B2

(12) United States Patent
Dove et al.

(10) Patent No.: US 11,864,893 B2
(45) Date of Patent: Jan. 9, 2024

(54) OXYGEN SENSOR CALIBRATION

(71) Applicant: Covidien LP, Mansfield, MA (US)

(72) Inventors: Jacob D. Dove, Lafayette, CO (US); Søren Aasmul, Holte (DK); William S. Smith, Wheat Ridge, CO (US); David J. Miller, Austin, TX (US); Jesper Svenning Kristensen, Virum (DK)

(73) Assignee: COVIDIEN LP, Mansfield, MA (US)

( * ) Notice: Subject to any disclaimer, the term of this patent is extended or adjusted under 35 U.S.C. 154(b) by 152 days.

(21) Appl. No.: 17/343,362

(22) Filed: Jun. 9, 2021

(65) Prior Publication Data

US 2022/0071517 A1 Mar. 10, 2022

Related U.S. Application Data

(60) Provisional application No. 63/074,763, filed on Sep. 4, 2020.

(51) Int. Cl.
*A61B 5/1495* (2006.01)
*A61B 5/145* (2006.01)
(Continued)

(52) U.S. Cl.
CPC ........ *A61B 5/1495* (2013.01); *A61B 5/14503* (2013.01); *A61B 5/14507* (2013.01);
(Continued)

(58) Field of Classification Search
CPC .............. A61B 5/1495; A61B 5/14503; A61B 5/14507; A61B 5/14542; A61B 5/207;
(Continued)

(56) References Cited

U.S. PATENT DOCUMENTS 4,462,246 A * 7/1984 Advani .............. G01N 33/0032
73/31.04
5,389,217 A 2/1995 Singer
(Continued)

FOREIGN PATENT DOCUMENTS

WO 2014/043650 A2 3/2014
WO 2017070155 A1 4/2017
(Continued)

OTHER PUBLICATIONS

International Search Report and Written Opinion of International Application No. PCT/US2021/048525, dated Jan. 4, 2022, 13 pp.
(Continued)

*Primary Examiner* — Matthew Kremer
*Assistant Examiner* — Kyle W. Kretzer
(74) *Attorney, Agent, or Firm* — Fletcher Yoder, P.C.

(57) ABSTRACT

An example device includes processing circuitry configured to receive, from an oxygen sensor, an ambient air signal indicative of an oxygen partial pressure of ambient air. The processing circuitry is further configured to receive, from an atmospheric pressure sensor, an atmospheric pressure sensor signal indicative of atmospheric pressure. The processing circuitry is configured to determine, based on the atmospheric pressure sensor signal, an oxygen partial pressure of the ambient air, determine, based at least in part on the oxygen partial pressure of the ambient air and the ambient air signal, the one or more calibration parameters, and calibrate, based on the one or more calibration parameters, the oxygen sensor. The calibrated oxygen sensor may be used to, for example, determine the oxygen content of urine of a patient to monitor renal function of the patient.

20 Claims, 6 Drawing Sheets

(51) Int. Cl.
*A61B 5/20* (2006.01)
*A61B 5/00* (2006.01)

(52) U.S. Cl.
CPC .......... *A61B 5/14542* (2013.01); *A61B 5/207* (2013.01); *A61B 5/6853* (2013.01); *A61B 2560/0223* (2013.01); *A61B 2560/0252* (2013.01); *A61B 2560/0257* (2013.01)

(58) Field of Classification Search
CPC .......... A61B 5/6853; A61B 2560/0223; A61B 2560/0257; A61B 5/201; A61B 2560/0252; G01N 27/4163; G01N 27/404
See application file for complete search history.

(56) References Cited

U.S. PATENT DOCUMENTS

| | | | |
|---|---|---|---|
| 5,609,824 | A | 3/1997 | Lauks et al. |
| 6,066,249 | A * | 5/2000 | Manzoni ............... G01N 33/96 204/415 |
| 8,663,128 | B2 | 3/2014 | Paz et al. |
| 9,662,058 | B2 | 5/2017 | Burnett et al. |
| 9,800,328 | B2 | 10/2017 | Mlekicki et al. |
| 10,391,275 | B2 | 8/2019 | Burnett et al. |
| 10,542,923 | B2 | 1/2020 | Chang et al. |
| 10,772,998 | B2 | 9/2020 | Luxon et al. |
| 11,583,232 | B2 | 2/2023 | Miller |
| 2006/0013744 | A1 | 1/2006 | Mikkelsen et al. |
| 2007/0232950 | A1 * | 10/2007 | West ...................... A61B 5/097 600/532 |
| 2016/0183819 | A1 | 6/2016 | Burnett et al. |
| 2016/0187258 | A1 * | 6/2016 | Mlekicki ............... G01N 21/274 250/206 |
| 2017/0136209 | A1 | 5/2017 | Burnett et al. |
| 2017/0347936 | A1 | 12/2017 | Stahmann et al. |
| 2018/0110455 | A1 | 4/2018 | Chang et al. |
| 2019/0069831 | A1 | 3/2019 | Kuck et al. |
| 2019/0343445 | A1 | 11/2019 | Burnett et al. |
| 2020/0022638 | A1 | 1/2020 | Suehara et al. |
| 2020/0170551 | A1 | 6/2020 | Horan et al. |
| 2020/0205718 | A1 | 7/2020 | Silverton et al. |
| 2020/0348275 | A1 * | 11/2020 | Mackenzie ............ G01N 21/63 |
| 2021/0031445 | A1 * | 2/2021 | Coeck ..................... B22F 10/31 |
| 2021/0186428 | A1 | 6/2021 | Miller |
| 2022/0071536 | A1 | 3/2022 | Dove et al. |
| 2022/0072270 | A1 | 3/2022 | Dove et al. |
| 2022/0076838 | A1 | 3/2022 | Dove et al. |

FOREIGN PATENT DOCUMENTS

| | | |
|---|---|---|
| WO | 2019/140224 A2 | 7/2019 |
| WO | 2019195028 A1 | 10/2019 |
| WO | 2022051550 A1 | 3/2022 |

OTHER PUBLICATIONS

Tosun et al., "Can Partial Oxygen Pressure of the Urine be an Indicator for Tissue Perfusion," AVES, Turkish Journal of Anaesthesiology and Reanimation, vol. 47, No. 3, doi:10.5152/TJAR.2019.89083, Jan. 29, 2019, pp. 187-191.

"Instruction Manual—Microx TX3—Software Version TX3v531," PreSens, Loligo, loligosystems.com, Mar. 2006, 89 pp.

Lankadeva et al., "Intrarenal and urinary oxygenation during norepinephrine resuscitation in ovine septic acute kidney injury," Elsevier, International Society of Nephrology, Kidney International, vol. 90, Apr. 16, 2016, pp. 100-108.

Sgouralis et al., "Bladder urine oxygen tension for assessing renal medullary oxygenation in rabbits: experimental and modeling studies," American Physiological Society, American Journal of Physiology—Regulatory, Integrative and Comparative Physiology, vol. 311, doi: 10.1152/ajpregu.00195.2016, Jul. 6, 2016, pp. R532-R544.

Zhu et al., "Urinary hypoxia: an intraoperative marker of risk of cardiac surgery-associated acute kidney injury," Advance Access, Nephrology Dialysis Transplantation, vol. 33, doi: 10.1093/ndt/gfy047, Mar. 14, 2018, pp. 2191-2201.

Evans et al., "Urinary oxygen tension: a clinical window on the health of the renal medulla," American Physiological Society, American Journal of Physiology—Regulatory, Integrative and Comparative Physiology, vol. 306, doi:10.1152?ajpregu.00437.2013, Nov. 13, 2013, pp. R45-R50.

U.S. Appl. No. 17/308,511, naming inventors Dove et al., filed May 5, 2021.

U.S. Appl. No. 17/410,834, naming inventors Dove et al., filed Aug. 24, 2021.

U.S. Appl. No. 17/466,488, naming inventors Dove et al., filed Sep. 3, 2021.

"Operating Principle and Construction of the Zirconium Dioxide Oxygen Sensors of the XYA Series," Sensor Technics, retrieved from https://s1.dtsheet.com/stor/data/001339331.pdf?key=e3f9d5aebb0a63bf6210e5b3f591c610&r=1, retrieved on Dec. 10, 2020, 9 pp.

"Control Systems/Estimators and Observers," Wikibooks, accessed from https://en.wikibooks.org/wiki/Control_Systems/Estimators_and_Observers, accessed on Aug. 30, 2023, 5 pp.

"Measuring Turbidity, TSS, and Water Clarity," accessed from. https://www.fondriest.com/environmental-measurements/measurements/measuring-water-quality/turbidity-sensors-meters-and-methods/, accessed on Aug. 30, 2023, 31 pp.

"Standard Performance Specification for Foley Catheter," ASTM International, accessed Sep. 30, 2019, 10 pp.

International Preliminary Report on Patentability from International Application No. PCT/US2021/048525 dated Mar. 16, 2023, 10 pp.

* cited by examiner

OXYGEN SENSOR CALIBRATION

This application claims the benefit of U.S. Provisional Application No. 63/074,763, entitled, "ACUTE KIDNEY INJURY MONITORING" and filed Sep. 4, 2020, the entire contents of which are hereby incorporated by reference.

TECHNICAL FIELD

This disclosure relates to calibrating an oxygen sensor for patient monitoring.

BACKGROUND

Medical devices, such as catheters, may be used to assist a patient in voiding their bladder. In some instances, such catheters may be used during and/or after surgery. In the case of using a catheter to assist a patient in voiding their bladder, a Foley catheter is a type of catheter that may be used for longer time periods than a non-Foley catheter. Some Foley catheters are constructed of silicon rubber and include an anchoring member, which may be an inflatable balloon, that may be inflated in a bladder of a patient so a proximal end of the catheter does not slip out of the bladder.

SUMMARY

In general, the disclosure describes devices, systems, and techniques for calibrating an oxygen sensor and for renal monitoring (also referred to herein as kidney function monitoring) of a patient based on an oxygen content of a fluid (e.g., urine) from the patient determined using the calibrated oxygen sensor. The oxygen content may be used to detect one or conditions indicative of acute kidney injury (AKI) of the patient or a risk the patient will develop AKI. The oxygen sensor may be used on its own or with other sensors, such as a temperature sensor or pressure sensor and may be used with a Foley catheter to sense a partial pressure of oxygen in a fluid, such as urine, in a lumen of the Foley catheter, distal to a distal end of the Foley catheter, or in a bladder of a patient.

In one example, a method includes receiving, by processing circuitry and from an oxygen sensor, an ambient air signal indicative of an oxygen partial pressure of ambient air; receiving, by the processing circuitry and from an atmospheric pressure sensor, an atmospheric pressure sensor signal indicative of atmospheric pressure; determining, by the processing circuitry and based on the atmospheric pressure sensor signal, an oxygen partial pressure of the ambient air; determining, by the processing circuitry and based at least in part on the oxygen partial pressure of the ambient air and the ambient air signal, one or more calibration parameters; and calibrating, by the processing circuitry and based on the one or more calibration parameters, the oxygen sensor.

In one example, a device includes memory configured to store one or more calibration parameters; and processing circuitry communicatively coupled to the memory, the processing circuitry being configured to: receive, from an oxygen sensor, an ambient air signal indicative of an oxygen partial pressure of ambient air; receive, from an atmospheric pressure sensor, an atmospheric pressure sensor signal indicative of atmospheric pressure; determine, based on the atmospheric pressure sensor signal, an oxygen partial pressure of the ambient air; determine, based at least in part on the oxygen partial pressure of the ambient air and the ambient air signal, the one or more calibration parameters; and calibrate, based on the one or more calibration parameters, the oxygen sensor.

In one example, a device includes memory configured to store one or more calibration parameters; and processing circuitry communicatively coupled to the memory, the processing circuitry being configured to: receive, from an oxygen sensor, an ambient air signal indicative of an oxygen partial pressure of ambient air; receive, from an atmospheric pressure sensor, an atmospheric pressure sensor signal indicative of atmospheric pressure; determine, based on the atmospheric pressure sensor signal, an oxygen partial pressure of the ambient air; determine, based at least in part on the oxygen partial pressure of the ambient air and the ambient air signal, the one or more calibration parameters; calibrate, based on the one or more calibration parameters, the oxygen sensor; receive, from the oxygen sensor, a signal indicative of an oxygen partial pressure of urine; and determine, based on the signal indicative of an oxygen partial pressure of the urine and the one or more calibration parameters, a calibrated oxygen partial pressure of the urine.

The details of one or more examples are set forth in the accompanying drawings and the description below. Other features, objects, and advantages will be apparent from the description and drawings, and from the claims.

DETAILED DESCRIPTION

Figure 1:
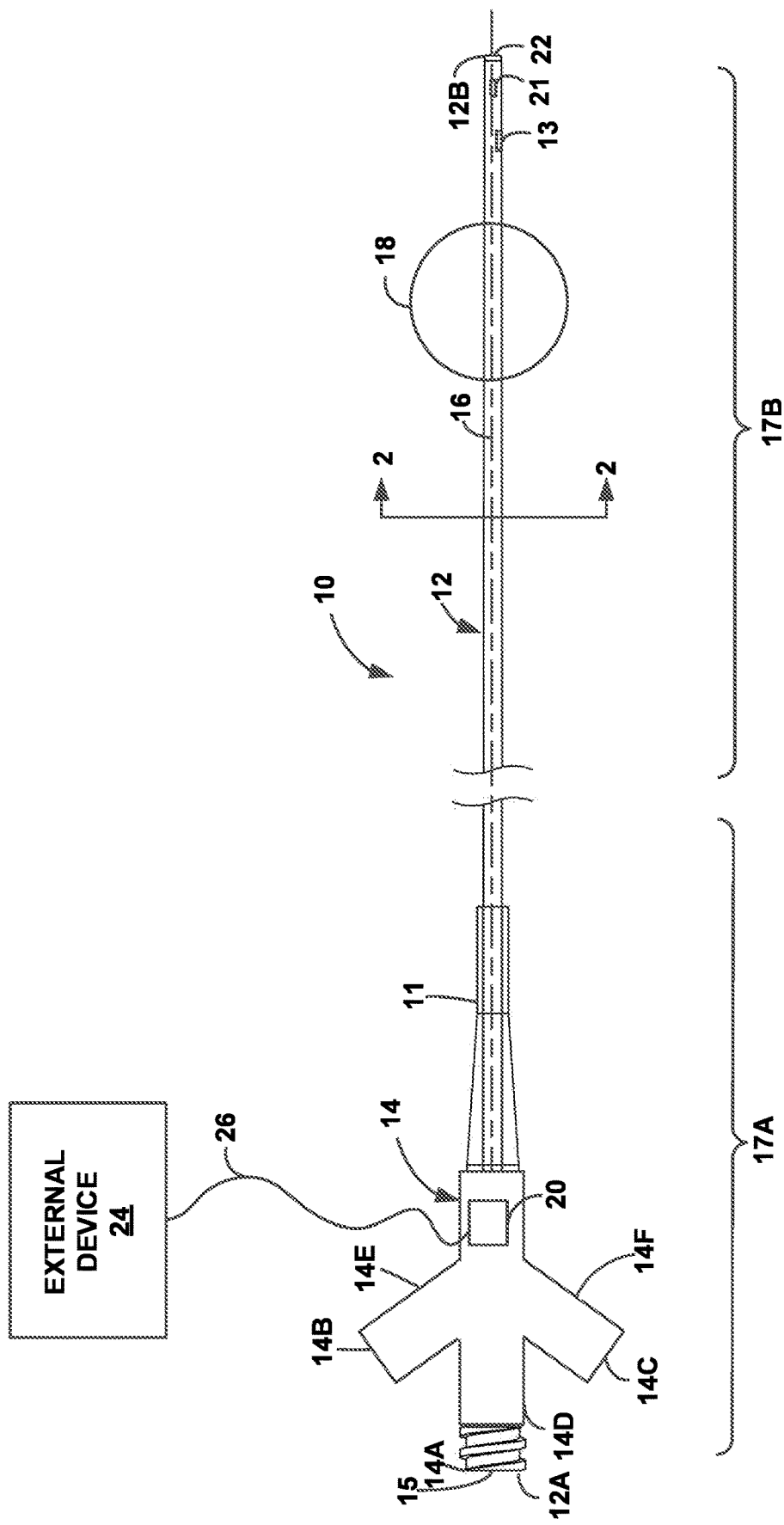
FIG. 1 is a diagram illustrating an example catheter.

Acute kidney injury (AKI) is a complication that may occur after some medical procedures, such as some cardiac surgeries, e.g., coronary artery bypass grafting (CABG). AKI may also occur after other surgeries that are lengthy and involve significant blood loss or fluid shifts. For example, a surgery patient's body may alter where their blood is directed which may lead to hypoxia of a kidney. A cause of surgery-associated AKI is hypoxia of the kidneys, which may cause an ischemia reperfusion injury in a kidney of the patient. This ischemia reperfusion injury may cause degradation of renal function of the patient. The degradation of renal function may cause an accumulation of waste products in the bloodstream, which may delay the patient's recovery from the surgery and lead to more extended hospital stays and may even lead to further complications.

The present disclosure describes example techniques, devices, and systems that are configured to monitor kidney function of patients, such as patients who are undergoing or who have undergone such surgeries, based on an oxygen content of a fluid (e.g., urine) removed from a bladder of the patient or in the bladder of the patient. The monitoring of kidney function may help reduce occurrences of AKI by providing clinicians with an assessment of the risk that a specific patient may develop AKI. This may facilitate a clinician intervening prior to the patient developing AKI. For example, a clinician may initiate or make changes to hemodynamic management (e.g., blood pressure management, fluid management, blood transfusions, and the like), make changes to cardiopulmonary bypass machine settings, or avoid providing nephrotoxic drugs. Post operatively, a clinician may intervene with a Kidney Disease: Improving Global Outcomes (KDIGO) bundle or an AKI care bundle, which may be predetermined set of guidelines and practices for the clinician to follow.

The devices and systems may include or be configured to communicate with one or more sensors configured to sense different parameters of a fluid of interest, such as urine in the case of kidney function monitoring. One or more of these sensors may be an oxygen sensor which may be calibrated according to the techniques of this disclosure. While urine, bladders, and AKI are primarily referred to herein to describe the example devices, in other examples, the devices may be used with other target locations in a patient, such as intravascular locations, and to monitor fluids of interest other than urine and/or other patient conditions other than kidney function.

While systemic vital signs like cardiac output, blood pressure, and hematocrit may be useful for monitoring the kidney function of a patient (also referred to herein as renal monitoring), it may also be useful to monitor the oxygenation status of the kidneys in order to limit, reduce the severity of, or even prevent the risk of AKI. The amount of dissolved oxygen in a urine of a patient may be indicative of kidney function or kidney health. Dissolved oxygen in a patient's urine and bladder may correlate to perfusion and/or oxygenation of the kidneys, which is indicative of kidney performance. Accurate monitoring of the oxygenation status of the kidneys can be challenging due to the inaccessibility of the kidneys. Near-Infrared spectroscopy (NIRS) measures regional oximetry, and has some utility in babies and relatively slender adults in measuring oxygenation of the kidneys, but may not have the depth of penetration and specificity required for some patients.

The present disclosure describes example medical devices, such as catheters, sensors and external devices, that are configured to sense and/or monitor kidney function of patients, such as patients who are undergoing or who have undergone surgeries or other medical procedures, which may help reduce occurrences of AKI. In some examples, the medical system includes at least one oxygen sensor configured to sense oxygen content in a fluid and generate a signal indicative of the oxygen content in the fluid. The oxygen content can indicate, for example, an amount of oxygen dissolved in the fluid (e.g., oxygen partial pressure ($pO_2$)). In some examples, the oxygen sensor may not be a part of the medical device. For example, the oxygen sensor may be distal to a distal end of the medical device or may be inserted into a lumen of the medical device or attached to the medical device. In some examples, the medical device includes the oxygen sensor. In any of these examples, however, the oxygen sensor can be configured to sense an amount of oxygen dissolved in urine in the bladder, in a lumen of the medical device, or distal to a distal end of the medical device. The signal from the oxygen sensor may enable a clinician or a device to determine the oxygenation status of one or both kidneys of the patient, particularly if the oxygen sensor is calibrated.

In some examples, an oxygen sensor may be temperature dependent. In other words, the temperature of the area around the oxygen sensor may impact an amount of oxygen sensed in the area around the oxygen sensor. Therefore, in some examples, the medical device also includes at least one temperature sensor. The inclusion of a temperature sensor may enable further calibration of the oxygen sensor based on sensed temperature, which may result in more accurate oxygen sensing by the oxygen sensor after calibration.

This disclosure also describes systems and techniques for calibrating the oxygen sensor. An uncalibrated or incorrectly calibrated oxygen sensor may incorrectly sense an amount of oxygen content in a fluid, such as urine. An incorrect measure of oxygen content in the fluid may lead to an incorrect determination of the risk that a patient may develop AKI. Calibrating the oxygen sensor may be desirable, as a calibrated oxygen sensor may provide a more accurate measurement of the oxygen content in the fluid, which may better enable a clinician to provide care to the patient to help minimize or even eliminate the risk of AKI.

While urine, bladders, and AKI are primarily referred to herein to describe the example medical devices, systems, and techniques, in other examples, the medical devices may be used with other target locations in a patient, such as intravascular locations, and to monitor fluids of interest other than urine and/or other patient conditions other than kidney function. In addition, while catheters are primarily referred to herein, in other examples, the medical device can have another configuration.

When monitoring kidney function of a patient, other parameters of interest may also be sensed. Examples of other parameters of interest sensed by a sensor described herein include, but are not limited to, any one or more of an urine flow rate, urine concentration, urine electrical conductivity, urine specific gravity, urine biomarkers, amount of dissolved carbon dioxide in the urine, urine pH, bladder or abdominal pressure, bladder temperature, urine color, urine turbidity, urine creatinine, urine electrical conductivity, urine sodium, or motion from an accelerometer or other motion sensor. In some cases, it may be desirable to sense one or more of these parameters relatively close to the kidneys as possible because when sensors are positioned further away from the kidneys, the risk of introducing noise or losing signal strength increases and/or the risk of the concentration or integrity of a substance of interest in the fluid of interest (e.g., urine) changing prior to being sensed by the sensor may increase.

In the case of a Foley catheter, it may be desirable to sense one or more of these parameters at the proximal end of the Foley catheter (e.g., in the bladder of the patient). However, placing these sensors at the proximal end of the catheter may increase the size and stiffness of the catheter and, as a result, may undermine the patient comfort or deliverability of the catheter. By design, a Foley catheter is configured to be small and flexible, such that it can be inserted through the urethra and into the bladder of a patient. If a Foley catheter were stiffer, then it may be more difficult to comfortably insert the catheter into the bladder of the patient. In some examples, an external device may estimate a parameter inside a patient's bladder based on sensing distal to the patient.

As used herein, "sense" may include detect and/or measure." As used herein, "proximal" is used as defined in Section 3.1.4 of ASTM F623-19, Standard Performance Specification for Foley Catheter. That is, the proximal end of a catheter is the end closest to the patient when the catheter is being used by the patient. The distal end is therefore the end furthest from the patient. In some examples, "block" may mean completely prevent or partially prevent (e.g., effectively prevent), such as by blocking, restricting, inhibiting, impeding, or hindering. For example, to block the flow of air through a gas tight compartment wall may mean that the air may not enter the compartment.

The amount of dissolved oxygen in a patient's urine may be indicative of kidney function or kidney health. For example, dissolved oxygen in a patient's urine in the bladder may correlate to perfusion and/or oxygenation of the kidneys, which is indicative of kidney performance. However, dissolved oxygen can be relatively difficult to measure. One way to measure dissolved oxygen is by a fluorescence or luminescence lifetime oxygen sensor(s). The oxygen sensor may utilize a light and sense the decay of glow from the light in a fluid, which may be indicative of the level of oxygen in the fluid. Utilizing the Stern-Volmer relationship, the partial pressure of oxygen in the fluid may be determined. For collision quenching, the Stern-Volmer relationship describes the relationship between the intensity and rate of decay of fluorescence (or phosphorescence) originating from the composition of the surrounding solution and changes therein. To more accurately measure the level of oxygen in a patient's urine, it may be desirable to calibrate the oxygen sensor prior to use. In some examples, oxygen sensors may be dependent on an altitude at which the oxygen sensors may be operating. Therefore, calibrating the oxygen sensor on-site, e.g., at the clinic at which the oxygen sensor is going to be used and relatively close in time to the use of the oxygen sensor, may provide a more accurate calibration than calibration at a manufacturing facility. The calibration devices, systems, and techniques described herein may better enable such on-site or timely calibration, which may result in more accurate determination of oxygen content in a fluid of interest by processing circuitry based on the signal generated by the oxygen sensor.

In some examples, rather than integrating all of the desired sensors in the proximal portion of an elongated body of a catheter (e.g., the portion that is to be inserted into the bladder of the patient or otherwise introduced in a patient), one or more sensors (e.g., an oxygen sensor and a temperature sensor) may be positioned anywhere along the elongated body (e.g., on the proximal portion or a distal portion) or distal to a distal end of the elongated body. The distal portion of the elongated body may include, for example, the portion intended to remain outside of the patient when the proximal portion is introduced in the patient. By locating sensors at the distal portion of the catheter or distal to a distal end of the elongated body, the sensors may be larger, may rely upon relatively more electrical and/or optical connections and the catheter itself may be smaller and more flexible than it would have been had all the sensors been positioned at the proximal portion of the catheter.

Example techniques and systems for calibrating an oxygen sensor are described herein. In some examples, processing circuitry is configured to receive, from an oxygen sensor, an ambient air signal indicative of an oxygen partial pressure of ambient air. The processing circuitry is configured to receive, from an atmospheric pressure sensor, an atmospheric pressure sensor signal indicative of atmospheric pressure. The processing circuitry is configured to determine, based on the atmospheric pressure sensor signal, an oxygen partial pressure of the ambient air and calibrate the oxygen sensor based at least in part on the oxygen partial pressure of the ambient air and the ambient air signal. In some examples, the device may also sense a temperature of the ambient air, or other gas of known oxygen concentration and the calibration may be further based on the sensed temperature. The sensed temperature may be useful in calibrating the oxygen sensor, as some oxygen sensors may be temperature dependent. In other words, the sensed oxygen content may be impacted by a temperature around the oxygen sensor.

In some examples, a kidney monitoring system includes an oxygen sensor that is calibrated according to the techniques described herein. The oxygen sensor may be calibrated prior to use in a patient, for example, when the oxygen sensor is located in ambient air. In some examples, the oxygen sensor is calibrated immediately before use in the patient.

FIG. 1 is a conceptual side elevation view of an example catheter 10, which includes elongated body 12, hub 14, and anchoring member 18. Catheter 10 may be used with one or more calibrated oxygen sensors to monitor the kidney function of a patient. In some examples, catheter 10 is a Foley catheter. While a Foley catheter and its intended use are primarily referred to herein to describe catheter 10, in other examples, catheter 10 can be used for other purposes, such as to drain wounds or for intravascular monitoring or medical procedures.

Catheter 10 includes a distal portion 17A and a proximal portion 17B. Distal portion 17A includes a distal end 12A of elongated body 12 and is intended to be external to a patient's body when in use, while proximal portion 17B includes a proximal end 12B of elongated body 12 and is intended to be internal to a patient's body when in use. For example, when proximal portion 17B is positioned within a patient, e.g., such that proximal end 12B of elongated body 12 is within the patient's bladder, distal portion 17A may remain outside of the body of the patient.

Elongated body 12 is a structure (e.g., a tubular structure) that extends from distal end 12A to proximal end 12B and defines one or more inner lumens. In the example shown in FIGS. 1-2, elongated body 12 defines lumen 32, drainage lumen 34 and anchoring lumen 36 (shown in FIG. 2). In other examples, elongated body 12 may define drainage lumen 34 and anchoring lumen 36, but not lumen 32. Other arrangements of lumens are also contemplated. In some examples, drainage lumen 34 is configured to drain a fluid from a target site, such as a bladder. In other examples drainage lumen 34 may be used for any other suitable purpose, such as to deliver a substance or another medical device to a target site within a patient. Drainage lumen 34 may extend from proximal fluid opening 13 to distal fluid opening 14A. Both fluid opening 13 and fluid opening 14A may be fluidically coupled to drainage lumen 34, such that a fluid may flow from one of fluid opening 13 or fluid opening 14A to the other of fluid opening 13 or fluid opening 14A through drainage lumen 34. Fluid opening 13 and fluid opening 14A may also be referred to as drainage openings.

In some examples, lumen 32 (shown in FIG. 2) may be an injection lumen configured to deliver a fluid to a target site, such as a bladder. In other examples, lumen 32 may be coupled to a pump (not shown), may house sensor 21, or may be used for any other suitable purpose, such as to deliver a medical device to a target site within a patient. Lumen 32 may extend from distal fluid opening 14C to proximal fluid opening 22. Both fluid opening 14C and fluid opening 22 may be fluidically coupled to lumen 32, such that a fluid may flow from one of fluid opening 14C or fluid opening 22 to the other of fluid opening 14C or fluid opening 22 through lumen 32. In the example where lumen 32 is an injection lumen, fluid opening 14C and fluid opening 22 may be injection openings. While fluid opening 22 is shown at the proximal end 12B of elongated body 12, fluid opening 22 may be positioned elsewhere on proximal portion 17B proximal to anchoring member 18.

In some examples, anchoring lumen 36 (shown in FIGS. 2) is configured to transport a fluid, such as sterile water or saline, or a gas, such as air, from anchoring opening 14B to anchoring member 18. For example, an inflation device (not shown) may deliver an inflation fluid or gas into anchoring lumen 36 through anchoring opening 14B into anchoring member 18 to expand anchoring member 18 to a size suitable to anchor catheter 10 within the bladder of a patient. In examples in which anchoring member 18 does not include an expandable balloon, rather than defining anchoring lumen 36, elongated body 12 may define an inner lumen configured to receive a deployment mechanism (e.g., a pull wire or a push wire) for deploying an expandable structure anchoring member 18 and hub 14 may comprise fluid opening 14A, fluid opening 14C, and anchoring opening 14B via which a clinician may access the deployment mechanism.

In some examples, elongated body 12 has a suitable length for accessing the bladder of a patient through the urethra. The length may be measured along central longitudinal axis 16 of elongated body 12. In some examples, elongated body 12 may have an outer diameter of about 12 French to about 14 French, but other dimensions may be used in other examples. Distal portion 17A and proximal portion 17B of elongated body 12 may each have any suitable length.

Elongated body 12 may be structurally configured to be relatively flexible, pushable, and relatively kink- and buckle-resistant, so that it may resist buckling when a pushing force is applied to a relatively distal portion of the medical device to advance the elongated body proximally through the urethra and into the bladder. Kinking and/or buckling of elongated body 12 may hinder a clinician's efforts to push the elongated body proximally.

In some examples, at least a portion of an outer surface of elongated body 12 includes one or more coatings, such as an anti-microbial coating, and/or a lubricating coating. The lubricating coating may be configured to reduce static friction and/or kinetic friction between elongated body 12 and tissue of the patient as elongated body 12 is advanced through the urethra.

In the example shown in FIG. 1, distal end 12A of elongated body 12 is received within hub 14 and is mechanically connected to hub 14 via an adhesive, welding, or another suitable technique or combination of techniques. Hub 14 is positioned at a distal end of elongated body 12 and defines an opening through which the one or more inner lumens (e.g., lumen 32, drainage lumen 34 and anchoring lumen 36, shown in FIG. 2) of elongated body 12 may be accessed and, in some examples, closed. While hub 14 is shown in FIG. 1 as having three arms, 14D, 14E and 14F, hub 14 may have any suitable number of arms, which may depend on the number of inner lumens defined by elongated body 12. For example, each arm may be fluidically coupled to a respective inner lumen of elongated body 12. In the example of FIG. 1, hub 14 comprises a fluid opening 14A, which is fluidically coupled to drainage lumen 34, anchoring opening 14B, which is fluidically coupled to anchoring lumen 36, and a fluid opening 14C which is fluidically coupled to lumen 32 (shown in FIGS. 2) of elongated body 12. In examples in which anchoring member 18 does not include an expandable balloon, rather than defining anchoring lumen 36, elongated body 12 may define an inner lumen configured to receive a deployment mechanism (e.g., a pull wire or a push wire) for deploying an expandable structure anchoring member 18 and hub 14 may comprise fluid opening 14A, fluid opening 14C and anchoring opening 14B via which a clinician may access the deployment mechanism.

In examples in which catheter 10 is a Foley catheter, a fluid collection container (e.g., a urine bag) may be attached to fluid opening 14A to collect urine draining from the patient's bladder. Anchoring opening 14B may be configured to connect to an inflation device to inflate or otherwise expand anchoring member 18 positioned on proximal portion 17B of catheter 10. Anchoring member 18 may be uninflated or otherwise undeployed when not in use. Hub 14 may include connectors, such as connector 15, for connecting to other devices, such as the fluid collection container and the inflation source. Fluid opening 14C may be configured to connect to an injection device or pull device, such as a pump, for introducing fluid into the patient's bladder or for pulling fluid out of patient's bladder, respectively. In some examples, catheter 10 includes strain relief member 11, which may be a part of hub 14 or may be separate from hub 14.

In some examples, sensor 20 is positioned on distal portion 17A of catheter 10, such as on hub 14. In some examples, sensor 20 is alternatively positioned distal to distal end 12A, such as on additional tubing or another structure connected to hub 14. Sensor 20 may be an oxygen sensor configured to sense a parameter of interest, such as dissolved oxygen, in a fluid, such as urine. In some examples, sensor 20 may also include a pressure sensor, such as an atmospheric pressure sensor. The fluid can be, for example, fluid in drainage lumen 34, fluid received from drainage lumen 34 or fluid in a bladder of a patient.

Proximal portion 17B of catheter 10 comprises anchoring member 18, fluid opening 13, fluid opening 22 and, in some examples, sensor 21. In some examples, sensor 21 is contained within lumen 32 or another lumen of elongated body 12. Anchoring member 18 may include any suitable structure configured to expand from a relatively low profile state to an expanded state in which anchoring member 18 may engage with tissue of a patient (e.g., inside a bladder) to help secure and prevent movement of proximal portion 17B out of the body of the patient. For example, anchoring member 18 can include an anchor balloon or other expandable structure. When inflated or deployed, anchoring member 18 may function to anchor catheter 10 to the patient, for example, within the patient's bladder. In this manner, the portion of catheter 10 on the proximal side of anchoring member 18 may not slip out of the patient's bladder. Fluid opening 13 may be positioned on the surface of elongated body 12 between anchoring member 18 and the proximal end 12B (as shown) or may be positioned at the proximal end 12B. Fluid opening 22 may be positioned at the proximal end 12B (as shown) of elongated body 12 or may be positioned on the surface of elongated body between anchoring member 18 and the proximal end 12B.

Sensor 20 is configured to sense a substance of interest (also referred to herein as a parameter of interest), for example dissolved oxygen, in a fluid, such as urine. Sensor 20 may be positioned on hub 14, as shown, or may be positioned elsewhere on distal portion 17A of the body of catheter 10, or may be positioned distal to distal end 12A, e.g., on tubing connected to a fluid collection container (e.g., a urine bag) or the like. Sensor 20, may be one or more sensors that are relatively larger, require relatively more electrical, optoelectrical, or optical connections, than sensors that could be located on the proximal portion 17B. While sensor 20 is primarily discussed herein as sensing dissolved oxygen and/or fluid output, in some examples, sensor 20 may additionally include sensor(s) configured to sense one or more of flow rate, temperature, pressure, fluid concentration, amount of dissolved carbon dioxide in the fluid, turbidity, fluid pH, fluid color, fluid creatinine, and/or motion.

In some examples, sensor 20 is mechanically connected to elongated body 12 or another part of catheter 10 using any suitable technique, such as, but not limited to, an adhesive, welding, by being embedded in elongated body 12, via a crimping band or another suitable attachment mechanism or combination of attachment mechanisms. As discussed above, in some examples, sensor 20 is not mechanically connected to elongated body 12 or catheter 10, but is instead mechanically connected to a structure that is distal to a distal end of catheter 10, such as to tubing that extends between hub 14 and a fluid collection container or inserted into a lumen of catheter 10. The calibration techniques described herein may be applied to sensors that are mechanically connected to elongated body 12 or another part of catheter 10 or to sensors that may be separate from elongated body 12 and another part of catheter 10. For example, the calibration techniques described herein may be used with a sensor that may be insertable into a lumen of elongated body 12 or between distal end 12A of elongated body 12 and a fluid collection bag, such as a urine bag.

Sensor 20 may be configured to communicate sensor data to external device 24. External device 24 may be a computing device, such as a workstation, a desktop computer, a laptop computer, a smart phone, a tablet, a server or any other type of computing device that may be configured to receive, process and/or display sensor data. Sensor 20 may communicate sensor data to the external device via a connection 26. Connection 26 may be an electrical, optical, wireless or other connection. In some examples, sensor 21 may also be configured to communicate sensor data to external device 24.

Although only sensor 20 and sensor 21 are shown in FIG. 1, in other examples, catheter 10 can include any suitable number of sensors on proximal portion 17B and any suitable number of sensors on distal portion 17A, where the sensors on proximal portion 17B sense the same or different parameters and the sensors on distal portion 17A sense the same or different parameters. In addition, some or all of the sensors on proximal portion 17B can sense the same or different parameters as the sensors on distal portion 17A. For example, in the case where sensors on the distal portion may be temperature dependent, it may be desirable to sense temperature both on the proximal portion 17B and the distal portion 17A. Alternatively, or additionally, a medical system may include one or more sensors configured to sense an oxygen content, a pressure and/or a temperature of a fluid, the one or more sensors being physically separate from catheter 10, such as one or more sensors that may be insertable into a lumen of elongated body 12 or between distal end 12A of elongated body 12 and a fluid collection bag, such as a urine bag.

Figure 2:
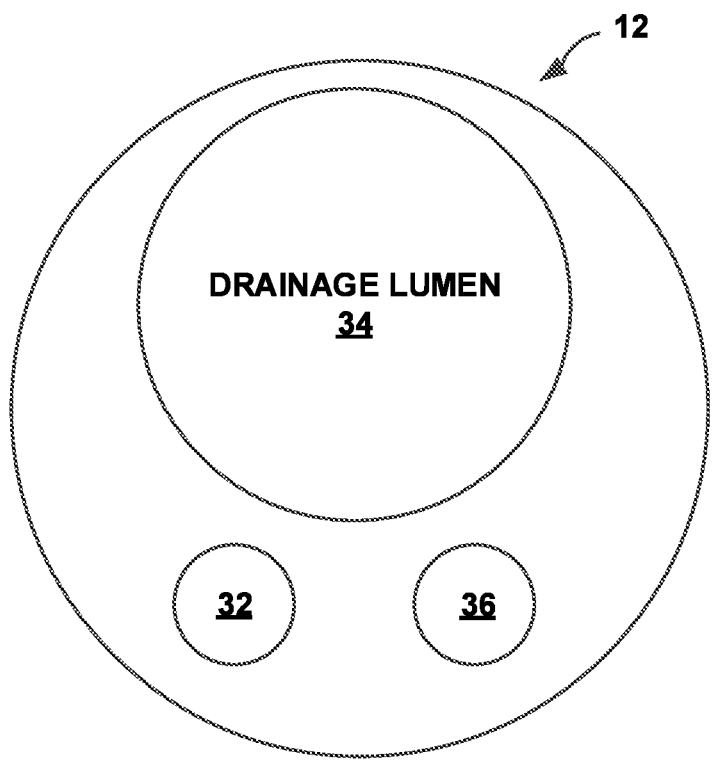
FIG. 2 is a diagram illustrating an example cross-sectional view of the catheter of FIG. 1, the cross-sections being taken along lines 2-2 of FIG. 1.

FIG. 2 is a diagram illustrating an example cross-section of elongated body 12 of catheter 10, where the cross-section is taken along line 2-2 in FIG. 1 in a direction orthogonal to central longitudinal axis 16. FIG. 2 depicts a cross section of elongated body 12, which defines lumen 32, drainage lumen 34, and anchoring lumen 36. While lumen 32, drainage lumen 34, and anchoring lumen 36 are shown as circular in cross-section, they may have any suitable cross-sectional shape in other examples.

Elongated body 12 can define any suitable number of lumens. For example, although one anchoring lumen 36 is shown in FIG. 2, in other examples, elongated body 12 can define a plurality of anchoring lumens 36, e.g., that are distributed around lumen 32 or drainage lumen 34. As another example, anchoring member 18 may be an expandable structure that is not an inflatable balloon. In such examples, anchoring lumen 36 may be replaced by a deployment mechanism which may permit a clinician to expand the expandable structure. For example, anchoring lumen 36 may be replaced by a mechanical device that may be pushed and pulled separately from the catheter 10 by a clinician to expand or retract the expandable structure. As another example of a different lumen configuration, in some examples, elongated body 12 may not include lumen 32 and can have only drainage lumen 34 and anchoring lumen 36.

Figure 3:
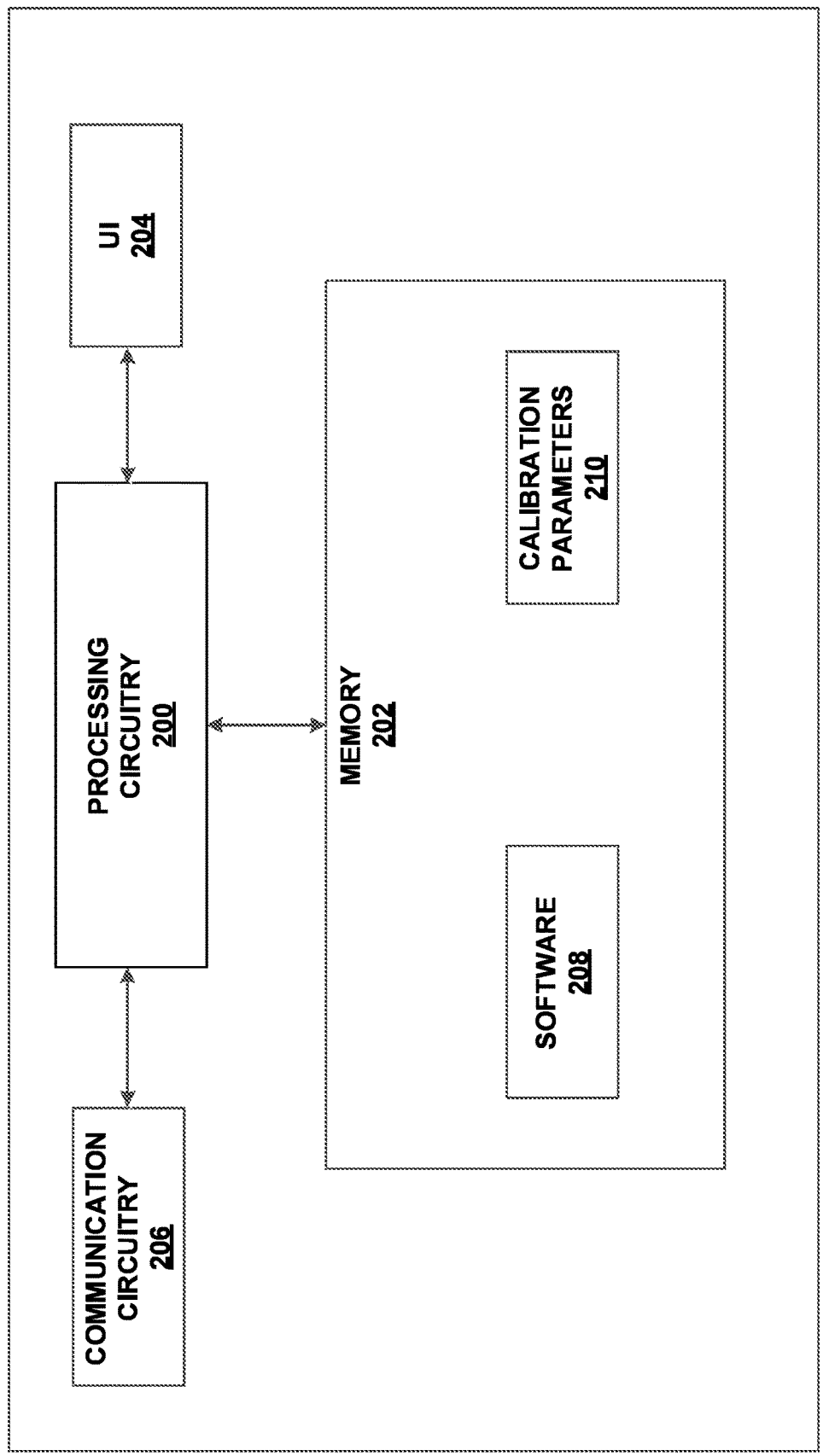
FIG. 3 is a block diagram of an example external device that may be used with a medical device according to example techniques of this disclosure.

FIG. 3 is a functional block diagram illustrating an example of an external device 24 configured to communicate with or receive information from sensor 20 (FIG. 1). In some examples, external device 24 also is configured to communicate with or receive information from sensor 21 (FIG. 1). In some examples, external device 24 may be configured to communicate with or receive information from an oxygen sensor to be calibrated, an atmospheric pressure sensor, and/or a temperature sensor, any of which may be sensor 20 or 21, or a sensor different from sensors 20, 21 and connected to catheter 10 or separate from catheter 10.

In the example of FIG. 3, external device 24 includes processing circuitry 200, memory 202, user interface (UI) 204, and communication circuitry 206. External device 24 may be a dedicated hardware device with dedicated software for the reading sensor data. Alternatively, external device 24 may be an off-the-shelf computing device, e.g., a desktop computer, a laptop computer, a tablet, or a smartphone running a mobile application that enables external device 24 to read sensor data from sensor 20.

In some examples, a user of external device 24 may be clinician, physician, or heath care giver. In some examples, a user uses external device 24 to calibrate the oxygen sensor and/or to monitor a patient's kidney function. In some examples, the user may interact with external device 24 via UI 204, which may include a display to present a graphical user interface to the user and/or sound generating circuitry configured to generate audio output, and a keypad or another mechanism (such as a touch sensitive screen) configured to receive input from the user. External device 24 may communicate with sensor 20 or sensor 21 using wired, wireless or optical methods through communication circuitry 206. For example, processing circuitry 200 of external device 24 may process sensor data from sensor 20 or sensor 21.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, such as software 208, which may include one or more program modules, which are executable by processing circuitry 200. When executed by processing circuitry 200, such program instructions may cause processing circuitry 200, and external device 24 to provide the functionality ascribed to them herein. The program instructions may be embodied in software and/or firmware.

Memory 202 may also store one or more calibration parameters 210. One or more calibration parameters 210 may include adjustments to be made to values of oxygen in a fluid by processing circuitry 200 based on a signal received from an oxygen sensor (e.g., sensor 20 or sensor 21). Such adjustments may improve the accuracy of sensed oxygen content in the fluid. One or more calibration parameters 210 may be determined via the techniques of this disclosure discussed in more detail with respect to FIGS. 4-6. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

This disclosure describes techniques and devices configured to aid in the monitoring of the one or both kidneys of a patient. In some examples, processing circuitry 200 of external device 24 monitors the amount of oxygen dissolved in the urine (e.g., $uPO_2$) in the bladder as it has been shown that this measurement reflects the oxygenation of the kidneys. To do this, the urine output (e.g., rate of urine production) and the amount of oxygen dissolved in the urine may be measured. Example techniques of this disclosure refer to the use of a catheter 10 (FIG. 1) and one or more sensors to make these measurements. In some examples, the sensors are part of the catheter 10. In other examples, the sensors are not part of the catheter 10. Such sensors may be calibrated according to the techniques of this disclosure to provide clinicians with more accurate measurements of the amount of dissolved oxygen in the urine.

Patients can be catheterized during and after major surgery using an indwelling urinary (Foley) catheter (e.g., catheter 10) inserted into the bladder via the urethra. Oxygen content of the urine of the patient may be measured at distal end 12A of the inserted catheter 10 using an oxygen sensor (e.g., sensor 20) inserted in the flow stream between the catheter and the urine collecting bag, in a lumen of the catheter, or near or at proximal end 12B of catheter 10 in the bladder of the patient. Such oxygen sensors may be used to monitor the kidney function of the patient.

Production variations in oxygen sensors may result in erroneous measurements if the oxygen sensors are not calibrated. Therefore, calibration for oxygen sensors for measuring oxygen partial pressure in urine may be useful or desirable. In some examples, external device 24 is configured to calibrate an oxygen sensor using at least a single point calibration for an offset calibration if the sensitivity slope or linearity of the output signal of oxygen sensor is predictable or known. In other examples, external device 24 may use a multiple-point calibration, such as a two-point calibration if an offset, as well as a sensitivity calibration, is desired.

Figure 4:
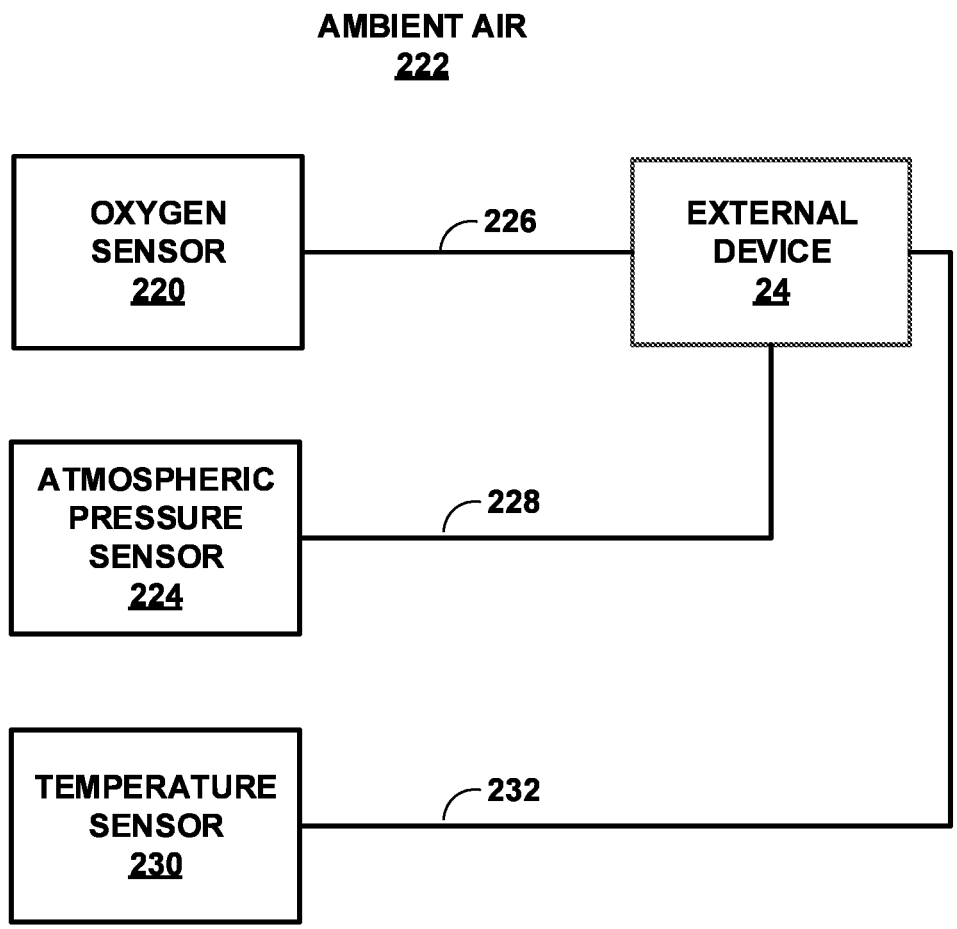
FIG. 4 is block diagram illustrating an example oxygen sensor calibration system according to techniques of this disclosure.

FIG. 4 is a block diagram illustrating an example oxygen sensor calibration system. In the example of FIG. 4, external device 24 may be communicatively coupled to oxygen sensor 220, which may be an example of sensor 20 or sensor 21 (both of FIG. 1), via connection 226. In other examples, oxygen sensor 220 may not be associated with catheter 10 and can be separate from catheter 10. External device 24 may also be communicatively coupled to atmospheric pressure sensor 224 via connection 228. In some examples, atmospheric pressure sensor 224 may be an example of sensor 20 or sensor 21. In other examples, atmospheric pressure sensor 224 may not be associated with catheter 10 and can be separate from catheter 10. In some examples, external device 24 may also be communicatively coupled to temperature sensor 230 via connection 232. In some examples, temperature sensor 230 may be an example of sensor 20 or sensor 21. In other examples, temperature sensor 230 may not be associated with catheter 10 and can be separate from catheter 10. While shown as separate sensors in FIG. 4, any of oxygen sensor 220, atmospheric pressure sensor 224, or temperature sensor 230 may be combined in to one sensor. By using an atmospheric pressure sensor signal, external device 24 may take advantage of the fact that there is a relatively stable partial pressure of oxygen in the atmosphere when external device 24 determines calibration parameters 210.

Connection 226, connection 228, or connection 232 may be an electrical, optical, wireless or other suitable connection. Connection 226 is configured to carry a signal (referred to herein as an ambient air signal) indicative of an oxygen partial pressure of ambient air 222 from oxygen sensor 220 to external device 24. Connection 228 is configured to carry a signal (referred to herein as an atmospheric pressure sensor signal) indicative of atmospheric pressure from atmospheric pressure sensor 224 to external device 24. Connection 232 is configured to carry a signal (referred to herein as a temperature sensor signal) indicative of a temperature of ambient air 222 from temperature sensor 230 to external device 24.

Processing circuitry 200 of external device 24 is configured to receive an ambient air signal from oxygen sensor 220, an atmospheric pressure sensor signal from atmospheric pressure sensor 224, and a temperature sensor signal from temperature sensor 230 via the respective connections 226, 228, 232, and calibrate oxygen sensor 220 based on the received signals. For example, processing circuitry 200 may determine calibration parameters 210 (FIG. 3) based on the received signals. In some examples, a user, such as a clinician, may expose oxygen sensor 220 to a known concentration of an analyte (in the example of FIG. 4, ambient air 222). Processing circuitry 200 may receive from oxygen sensor 220 an ambient air signal indicative of an oxygen partial pressure of ambient air. Processing circuitry 200 may also receive from atmospheric pressure sensor 224, an atmospheric pressure sensor signal indicative of atmospheric pressure. Processing circuitry 200 may determine a true partial pressure of oxygen of the analyte and compare the indicated oxygen partial pressure of the analyte from oxygen sensor 220 to the determined true oxygen partial pressure of the analyte. Based on the comparison, processing circuitry 200 may determine one or more calibration parameters 210 which processing circuitry 200 may use to reduce or minimize any error in the signal from oxygen sensor 220. Such a calibration technique may be simpler and more cost effective than traditional calibration techniques that may use four mixed gases in a predetermined ratio.

For example, for a single point calibration, oxygen sensor 220 may sense oxygen partial pressure while oxygen sensor 220 is exposed to ambient air 222. The oxygen partial pressure of ambient air can be generally around 20.9 percent in some cases, but may be affected by atmospheric pressure. As atmospheric pressure may change at different elevations and atmospheric conditions, it may be desirable to obtain a measure of atmospheric pressure to determine the true oxygen partial pressure of ambient air when calibrating oxygen sensor 220. Therefore, based on a sensed atmospheric pressure signal from atmospheric pressure sensor 224, processing circuitry 200 can determine the true oxygen partial pressure of ambient air 222. For example, processing circuitry 200 may determine, based on the atmospheric pressure sensor signal, an oxygen partial pressure of ambient air 222. Processing circuitry 200 may determine, based at least in part on the oxygen partial pressure of ambient air 222 and the ambient air signal from oxygen sensor 220, one or more calibration parameters 210. Processing circuitry 200 may calibrate, based on one or more calibration parameters 210, oxygen sensor 220.

For example, the atmospheric pressure at sea-level is approximately 760 mmHg. If oxygen sensor 220 is being calibrated at sea-level, then the atmospheric pressure sensor signal is indicative of the atmospheric pressure being 760 mmHg. Processing circuitry 200 may determine the true oxygen partial pressure of ambient air 222 to be 20.9 percent of 760 mmHg or 158.84 mmHg. If the ambient air signal is indicative of an oxygen partial pressure of ambient air 222 being 160.84 mmHg, then processing circuitry 200 may determine an offset of −2 for oxygen sensor 220 as a calibration parameter. If the ambient air signal is indicative of an oxygen partial pressure of ambient air 222 being 156.84, then processing circuitry 200 may determine an offset of +2 for oxygen sensor 220 as a calibration parameter. Alternatively, or in addition, processing circuitry 200 may determine a slope between the indication of the ambient air signal and the indication of the atmospheric pressure sensor signal. For example, processing circuitry 200 may determine a slope of the change between 158.84 and 160.84 for the first case, or between 158.84 and 156.84 for the second case. In some examples, rather than determine a calibration parameter from a single sensing, processing circuitry 200 may make a plurality of determinations over a time period and average those determinations to determine a calibration parameter. In order to obtain high accuracy of the sensor after the calibration the local ambient pressure may be determined by the use of an internal or external barometer.

If oxygen sensor 220 is temperature sensitive, then processing circuitry 200 of external device 24 may also determine the temperature of the environment in which oxygen sensor 220 is being used based on a temperature sensor signal generated by temperature sensor 230 and calibrate oxygen sensor 220 further based on the temperature sensor signal. In some examples, atmospheric pressure sensor 224 and/or temperature sensor 230 may be part of oxygen sensor 220.

In some examples, processing circuitry 200 determines, based at least in part on the oxygen partial pressure of ambient air 222 (determined based on the atmospheric pressure sensor signal) and the ambient air signal from oxygen sensor 220, one or more calibration parameters 210 for oxygen sensor 220. After determining one or more calibration parameters 210, processing circuitry 200 may determine an oxygen partial pressure in a fluid (e.g., urine) based on a fluid signal from oxygen sensor 222 and apply a function to the determined oxygen partial pressure, wherein the function is based on one or more calibration parameters 210. In some examples, the function is the one or more calibration parameters 210. In some examples, the function is an offset which processing circuitry 200 may add to or subtract from the determined oxygen partial pressure in the fluid (determined based on an oxygen sensor signal from oxygen sensor 220). Processing circuitry 200 may display the resulting calibrated measurement of oxygen in the fluid on UI 204 or an external display. In some examples, the calibrated measurement of oxygen in the fluid may be used to monitor a patient for AKI, which may facilitate or lead to earlier treatment, or to determine a risk of a patient developing AKI. For example, processing circuitry 200 may implement the techniques of U.S. patent application Ser. No. 17/308,511 filed on May 5, 2021, which is hereby incorporated by reference in its entirety.

Figure 5:
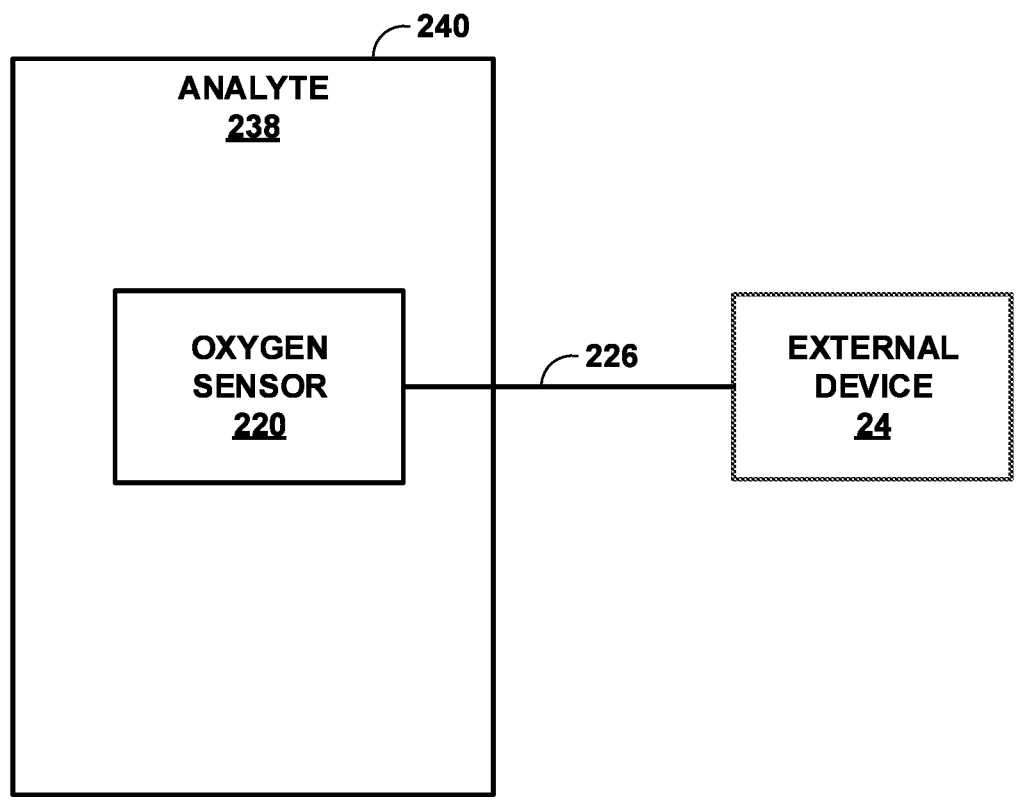
FIG. 5 is block diagram illustrating an example oxygen sensor calibration system according to techniques of this disclosure.

FIG. 5 is block diagram illustrating an example calibration system configured to conduct a two-point calibration of oxygen sensor 220. The two-point calibration can be a calibration performed by processing circuitry 200 in addition to the calibration discussed with respect to FIG. 4. The two point calibration may be performed before or after the calibration of FIG. 4.

In the example shown in FIG. 5, oxygen sensor 220 is packed with an analyte, such as a gas having a known oxygen partial pressure, in gas tight container 240, such as a pouch or bag. Gas tight container 240 has a structured configured to substantially block (e.g., completely block or nearly completely block to the extent permitted by manufacturing tolerances) ambient air 222 from entering gas tight container 240. In some examples, gas tight container 240 may be shipping or storage packaging for oxygen sensor 220. In some examples, gas tight container 240 may be a polystyrene bag or aluminum foil container. For example, a clinician or manufacturer may position oxygen sensor 220 in a nitrogen or a carbon dioxide ($CO_2$) atmosphere in gas tight container 240 which constitutes an oxygen partial pressure of zero and is relatively easy to control in addition to also forming an inert environment that may preserve oxygen sensor 220, e.g., during transport and storage of oxygen sensor 220. While all of oxygen sensor 220 is shown in gas tight container 240, in some examples, only a portion of oxygen sensor 220 is within gas tight container 240, such as the oxygen sensitive part of oxygen sensor 220.

Processing circuitry 200 conducts a calibration measurement while the oxygen sensitive part of oxygen sensor 220 is still inside gas tight container 240. For example, processing circuitry 200 may receive, from oxygen sensor 220, a signal from oxygen sensor 220 (referred to herein as an analyte signal) indicative of an oxygen partial pressure of analyte 238. In this example, one or more calibration parameters may be further based on the analyte signal. Processing circuitry 200 may calibrate oxygen sensor 220 based on the one or more calibration parameters 210. For example, processing circuitry 200 may determine one or more calibration parameters 210, which may be a function. In some examples, the function is a linear function. In some examples, the function is based on the Stern-Volmer relationship.

In some examples, processing circuitry 200 may also calibrate oxygen sensor 220 using the one point calibration technique and system described with respect to FIG. 4 may be made once the oxygen sensitive part of oxygen sensor 220 is removed from the gas tight compartment and exposed ambient environment.

For example, as discussed with respect to FIG. 4, in one example, processing circuitry 200 may determine the ambient air signal to be indicative of an oxygen partial pressure of ambient air 222 at sea-level to be 156.84 mmHg, which may be 2 mmHg under the true oxygen partial pressure of ambient air 222. In an example, processing circuitry 200 may also determine the analyte signal to be indicative of an oxygen partial pressure of analyte 238 (e.g., pure nitrogen or carbon dioxide) to be 3 mmHg, which would be 3 mmHg higher than the true oxygen partial pressure of analyte 238. In this example, processing circuitry 200 may determine a calibration parameter to be linear function between −3 mmHg at a sensed oxygen partial pressure of 3 mmHg and a +2 mmHg at a sensed oxygen partial pressure of 156.84.

For example, processing circuitry 200 may use the linear function as an offset to cancel out offset error.

Figure 6:
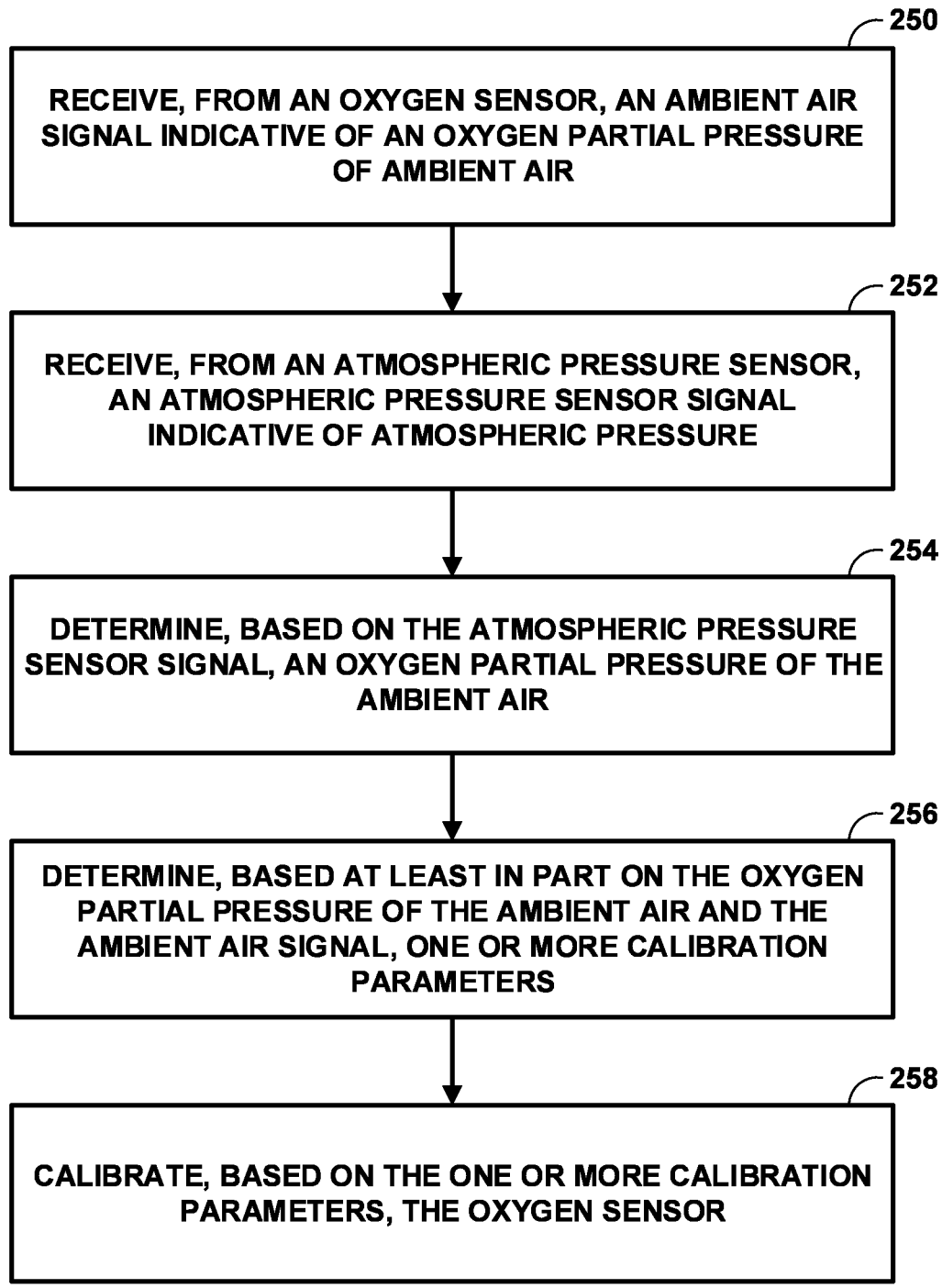
FIG. 6 is a flow diagram illustrating example oxygen sensor calibration techniques according to this disclosure.

FIG. 6 is a flow diagram illustrating example oxygen sensor calibration techniques. Processing circuitry 200 receives, from oxygen sensor 220, an ambient air signal indicative of an oxygen partial pressure of ambient air (250). For example, communication circuitry 206 of external device 24 may receive the ambient air signal from oxygen sensor 220 via connection 226. Processing circuitry 200 may then receive the ambient air signal from communication circuitry 206.

Processing circuitry 200 receives, from atmospheric pressure sensor 224, an atmospheric pressure sensor signal indicative of atmospheric pressure (252). For example, communication circuitry 206 of external device 24 may receive the atmospheric pressure sensor signal from atmospheric pressure sensor 224 via connection 228. Processing circuitry 200 may then receive the atmospheric pressure sensor signal from communication circuitry 206.

Processing circuitry 200 determines, based on the atmospheric pressure sensor signal, an oxygen partial pressure of the ambient air (254). For example, processing circuitry 200 may calculate an oxygen partial pressure of the ambient air based on the atmospheric pressure sensor signal, as the relationship between atmospheric pressure and oxygen partial pressure in the atmosphere (e.g., ambient air 222) is known. For example, if the actual atmospheric pressure is known, the actual oxygen partial pressure in the atmosphere may be determined.

Processing circuitry 200 determines, based at least in part on the oxygen partial pressure of the ambient air and the ambient air signal, one or more calibration parameters 210 (256). For example, processing circuitry 200 may determine a function or offset based on the determined oxygen partial pressure of the ambient air and the ambient air signal from oxygen sensor 220 and store the function or offset in memory 202.

Processing circuitry 200 may calibrate, based on one or more calibration parameters 210, oxygen sensor 220 (258). For example, processing circuitry 200 may apply the function or offset to a measurement from oxygen sensor 220 to calibrate oxygen sensor 220.

For example, as part of calibrating oxygen sensor 220, processing circuitry 200 may determine an oxygen partial pressure in a fluid based on a fluid signal from oxygen sensor 220 and apply a function to the determined oxygen partial pressure, wherein the function is based on one or more calibration parameters 210. In other words, processing circuitry 200 may determine an oxygen content in a fluid based on a signal from oxygen sensor 220 and apply one or more calibration parameters 210 to the signal to determine a calibrated oxygen partial pressure in the fluid. In some examples, the function is an offset.

In some examples, processing circuitry 200 receives, from temperature sensor 230, a temperature sensor signal indicative of a temperature of ambient air 222. In such examples, one or more calibration parameters 210 are further based on the temperature sensor signal. For example, a temperature dependency of an oxygen sensor may be determined in a laboratory. A laboratory technician or scientist may test the oxygen sensor at different temperatures when sensing an analyte of known oxygen content. The resulting test data may be used to generate a temperature offset or function which processing circuitry 200 may apply when calibrating oxygen sensor 220. In some examples, this temperature offset or function may be stored as part of calibration parameters 210. In some examples, the temperature offset or function may be implemented in a lookup table in memory 202.

In some examples, e.g., a described with reference to FIG. 5, processing circuitry 200 may receive, from oxygen sensor 220, an analyte signal indicative of an oxygen partial pressure of analyte 238. In such examples, one or more calibration parameters 210 may be further based on the analyte signal, as discussed above. In some examples, the analyte is nitrogen or carbon dioxide. In some examples, oxygen sensor 220 is located in gas tight container 240 when sensing the oxygen partial pressure of analyte 238.

In some examples, as part of calibrating oxygen sensor 220, processing circuitry 200 may determine an oxygen partial pressure in a fluid based on a fluid signal from oxygen sensor 220 and apply a function to the determined oxygen partial pressure. In some examples, the function is based on one or more calibration parameters 210 and one or more calibration parameters 210 are further based on the analyte signal. In some examples, the function is a linear function. In some examples, the function is based on a Stern-Volmer relationship. In some examples, processing circuitry 200 may receive, from oxygen sensor 220, a signal indicative of an oxygen partial pressure of urine and determine, based on the signal indicative of an oxygen partial pressure of the urine and one or more calibration parameters 210, a calibrated oxygen partial pressure of the urine.

Any of the techniques or examples described herein may be used alone or in combination with one or more other techniques or examples.

The techniques described in this disclosure, including those attributed to sensor 20, sensor 21, processing circuitry 200, communication circuitry 206, and UI 204 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

This disclosure includes the following non-limiting examples.

Example 1. A method comprising: receiving, by processing circuitry and from an oxygen sensor, an ambient air signal indicative of an oxygen partial pressure of ambient air; receiving, by the processing circuitry and from an atmospheric pressure sensor, an atmospheric pressure sensor signal indicative of atmospheric pressure; determining, by the processing circuitry and based on the atmospheric pressure sensor signal, an oxygen partial pressure of the ambient air; determining, by the processing circuitry and based at least in part on the oxygen partial pressure of the ambient air and the ambient air signal, one or more calibration parameters; and calibrating, by the processing circuitry and based on the one or more calibration parameters, the oxygen sensor.

Example 2. The method of example 1, wherein calibrating the oxygen sensor comprises: determining, by the processing circuitry, an oxygen partial pressure in a fluid based on a fluid signal from the oxygen sensor; and applying, by the processing circuitry, a function to the determined oxygen partial pressure, wherein the function is based on the one or more calibration parameters.

Example 3. The method of example 2, wherein the function is an offset.

Example 4. The method of any combination of examples 1-3, further comprising: receiving, by the processing circuitry and from a temperature sensor, a temperature sensor signal indicative of a temperature of the ambient air, wherein the one or more calibration parameters are further based on the temperature sensor signal.

Example 5. The method of any combination of examples 1-4, further comprising: receiving, by the processing circuitry and from the oxygen sensor, an analyte signal indicative of an oxygen partial pressure of an analyte, wherein the one or more calibration parameters are further based on the analyte signal.

Example 6. The method of example 5, wherein the analyte is nitrogen or carbon dioxide.

Example 7. The method of example 5 or example 6, wherein the oxygen sensor is located in a gas tight container when sensing the oxygen partial pressure of the analyte.

Example 8. The method of any combination of examples 5-7, wherein calibrating the oxygen sensor comprises: determining, by the processing circuitry, an oxygen partial pressure in a fluid based on a fluid signal from the oxygen sensor; and applying a function to the determined oxygen partial pressure, wherein the function is based on the one or more calibration parameters, and the one or more calibration parameters are further based on the analyte signal.

Example 9. The method of example 8, wherein the function comprises a linear function.

Example 10. The method of example 8, wherein the function is based on a Stern-Volmer relationship.

Example 11. A device comprising: memory configured to store one or more calibration parameters; and processing circuitry communicatively coupled to the memory, the processing circuitry being configured to: receive, from an oxygen sensor, an ambient air signal indicative of an oxygen partial pressure of ambient air; receive, from an atmospheric pressure sensor, an atmospheric pressure sensor signal indicative of atmospheric pressure; determine, based on the atmospheric pressure sensor signal, an oxygen partial pressure of the ambient air; determine, based at least in part on the oxygen partial pressure of the ambient air and the ambient air signal, the one or more calibration parameters; and calibrate, based on the one or more calibration parameters, the oxygen sensor.

Example 12. The device of example 11, wherein as part of calibrating the oxygen sensor, the processing circuitry is configured to: determine an oxygen partial pressure in a fluid based on a fluid signal from the oxygen sensor; and apply a function to the determined oxygen partial pressure, wherein the function is based on the one or more calibration parameters.

Example 13. The device of example 12, wherein the function is an offset.

Example 14. The device of any combination of examples 11-13, wherein the processing circuitry is further configured to: receive, from a temperature sensor, a temperature sensor signal indicative of a temperature of the ambient air, wherein the one or more calibration parameters are further based on the temperature sensor signal.

Example 15. The device of any combination of examples 11-14, wherein the processing circuitry is further configured to: receive, from the oxygen sensor, an analyte signal indicative of an oxygen partial pressure of an analyte, wherein the one or more calibration parameters are further based on the analyte signal.

Example 16. The device of example 15, wherein the analyte is nitrogen or carbon dioxide.

Example 17. The device of example 15 or example 16, wherein the oxygen sensor is located in a gas tight container when sensing the oxygen partial pressure of the analyte.

Example 18. The device of any combination of examples 15-17, wherein as part of calibrating the oxygen sensor, the processing circuitry is configured to: determine an oxygen partial pressure in a fluid based on a fluid signal from the oxygen sensor; and apply a function to the determined oxygen partial pressure, wherein the function is based on the one or more calibration parameters, and the one or more calibration parameters are further based on the analyte signal.

Example 19. The device of example 18, wherein the function comprises a linear function.

Example 20. A device comprising: memory configured to store one or more calibration parameters; and processing circuitry communicatively coupled to the memory, the processing circuitry being configured to: receive, from an oxygen sensor, an ambient air signal indicative of an oxygen partial pressure of ambient air; receive, from an atmospheric pressure sensor, an atmospheric pressure sensor signal indicative of atmospheric pressure; determine, based on the atmospheric pressure sensor signal, an oxygen partial pressure of the ambient air; determine, based at least in part on the oxygen partial pressure of the ambient air and the ambient air signal, the one or more calibration parameters; calibrate, based on the one or more calibration parameters, the oxygen sensor; receive, from the oxygen sensor, a signal indicative of an oxygen partial pressure of urine; and determine, based on the signal indicative of an oxygen partial pressure of the urine and the one or more calibration parameters, a calibrated oxygen partial pressure of the urine.

Various examples have been described. These and other examples are within the scope of the following claims.

What is claimed is:

1. A method comprising:
receiving, by processing circuitry and from an oxygen sensor, an ambient air signal indicative of an oxygen partial pressure of ambient air;
receiving, by the processing circuitry and from an atmospheric pressure sensor, an atmospheric pressure sensor signal indicative of atmospheric pressure;
determining, by the processing circuitry and based on the atmospheric pressure sensor signal, the oxygen partial pressure of the ambient air;
determining, by the processing circuitry and based at least in part on the oxygen partial pressure of the ambient air and the ambient air signal, one or more calibration parameters;
calibrating, by the processing circuitry and based on the one or more calibration parameters, the oxygen sensor;
receiving, by the processing circuitry and from the oxygen sensor, a signal indicative of an oxygen partial pressure of a fluid; and
determining, by the processing circuitry and based on the signal indicative of the oxygen partial pressure of the fluid and the one or more calibration parameters, a calibrated oxygen partial pressure of the fluid.

2. The method of claim 1, wherein determining the calibrated oxygen partial pressure of the fluid comprises:
determining, by the processing circuitry, the oxygen partial pressure of the fluid based on the signal indicative of the oxygen partial pressure of the fluid; and
applying, by the processing circuitry, a function to the determined oxygen partial pressure of the fluid, wherein the function is based on the one or more calibration parameters.

3. The method of claim 2, wherein the function is an offset.

4. The method of claim 1, further comprising:
receiving, by the processing circuitry and from a temperature sensor, a temperature sensor signal indicative of a temperature of the ambient air,
wherein the one or more calibration parameters are further based on the temperature sensor signal.

5. The method of claim 1, further comprising:
receiving, by the processing circuitry and from the oxygen sensor, an analyte signal indicative of an oxygen partial pressure of an analyte,
wherein the one or more calibration parameters are further based on the analyte signal.

6. The method of claim 5, wherein the analyte is nitrogen or carbon dioxide.

7. The method of claim 5, wherein the oxygen sensor is located in a gas tight container when sensing the oxygen partial pressure of the analyte.

8. The method of claim 5, wherein determining the calibrated oxygen partial pressure of the fluid comprises:
determining, by the processing circuitry, the oxygen partial pressure of the fluid based on the signal indicative of the oxygen partial pressure of the fluid; and
applying a function to the determined oxygen partial pressure of the fluid, wherein the function is based on the one or more calibration parameters, and the one or more calibration parameters are further based on the analyte signal.

9. The method of claim 8, wherein the function comprises a linear function.

10. The method of claim 8, wherein the function is based on a Stern-Volmer relationship.

11. A device comprising:
a memory configured to store one or more calibration parameters; and
processing circuitry communicatively coupled to the memory, the processing circuitry being configured to:
receive, from an oxygen sensor, an ambient air signal indicative of an oxygen partial pressure of ambient air;
receive, from an atmospheric pressure sensor, an atmospheric pressure sensor signal indicative of atmospheric pressure;
determine, based on the atmospheric pressure sensor signal, the oxygen partial pressure of the ambient air;
determine, based at least in part on the oxygen partial pressure of the ambient air and the ambient air signal, the one or more calibration parameters; and
calibrate, based on the one or more calibration parameters, the oxygen sensor,
receive, from the oxygen sensor, a signal indicative of an oxygen partial pressure of a fluid; and
determine, based on the signal indicative of the oxygen partial pressure of the fluid and the one or more calibration parameters, a calibrated oxygen partial pressure of the fluid.

12. The device of claim 11, wherein as part of determining the calibrated oxygen partial pressure of the fluid, the processing circuitry is configured to:
determine the oxygen partial pressure of the fluid based on the signal indicative of the oxygen partial pressure of the fluid; and
apply a function to the determined oxygen partial pressure of the fluid, wherein the function is based on the one or more calibration parameters.

13. The device of claim 12, wherein the function is an offset.

14. The device of claim 11, wherein the processing circuitry is further configured to:
receive, from a temperature sensor, a temperature sensor signal indicative of a temperature of the ambient air,
wherein the one or more calibration parameters are further based on the temperature sensor signal.

15. The device of claim 11, wherein the processing circuitry is further configured to:
receive, from the oxygen sensor, an analyte signal indicative of an oxygen partial pressure of an analyte,
wherein the one or more calibration parameters are further based on the analyte signal.

16. The device of claim 15, wherein the analyte is nitrogen or carbon dioxide.

17. The device of claim 15, wherein the oxygen sensor is configured to sense the oxygen partial pressure of the analyte when the oxygen sensor is located in a gas tight container.

18. The device of claim 15, wherein as part of determining the calibrated oxygen partial pressure of the fluid, the processing circuitry is configured to:
determine the oxygen partial pressure of the fluid based on the signal indicative of the oxygen partial pressure of the fluid; and
apply a function to the determined oxygen partial pressure of the fluid, wherein the function is based on the one or more calibration parameters, and the one or more calibration parameters are further based on the analyte signal.

19. The device of claim 18, wherein the function comprises a linear function.

20. A device comprising:
a memory configured to store one or more calibration parameters; and
processing circuitry communicatively coupled to the memory, the processing circuitry being configured to:
receive, from an oxygen sensor, an ambient air signal indicative of an oxygen partial pressure of ambient air;
receive, from an atmospheric pressure sensor, an atmospheric pressure sensor signal indicative of atmospheric pressure;
determine, based on the atmospheric pressure sensor signal, the oxygen partial pressure of the ambient air;
determine, based at least in part on the oxygen partial pressure of the ambient air and the ambient air signal, the one or more calibration parameters;
calibrate, based on the one or more calibration parameters, the oxygen sensor;
receive, from the oxygen sensor, a signal indicative of an oxygen partial pressure of urine; and
determine, based on the signal indicative of the oxygen partial pressure of the urine and the one or more calibration parameters, a calibrated oxygen partial pressure of the urine.

\* \* \* \* \*